United States Patent
Kim et al.

(10) Patent No.: US 9,766,194 B2
(45) Date of Patent: Sep. 19, 2017

(54) METHOD FOR MANAGING TEMPERATURE ANOMALY IN HYDROGEN TANK, AND SYSTEM FOR MONITORING TEMPERATURES IN SAME

(71) Applicant: Hyundai Motor Company, Seoul (KR)

(72) Inventors: Hyung-Ki Kim, Seoul (KR); Chang-Ho Kim, Gyeonggi-do (KR); Ji-Hyun Shim, Seoul (KR)

(73) Assignee: Hyundai Motor Company, Seoul (KR)

( * ) Notice: Subject to any disclaimer, the term of this patent is extended or adjusted under 35 U.S.C. 154(b) by 602 days.

(21) Appl. No.: 14/256,328

(22) Filed: Apr. 18, 2014

(65) Prior Publication Data

US 2015/0139268 A1 May 21, 2015

(30) Foreign Application Priority Data

Nov. 15, 2013 (KR) .................. 10-2013-0139062

(51) Int. Cl.
*G01N 25/72* (2006.01)
*G01K 15/00* (2006.01)
(Continued)

(52) U.S. Cl.
CPC ........... *G01N 25/72* (2013.01); *F17C 13/026* (2013.01); *F17C 2205/013* (2013.01); *F17C 2221/012* (2013.01); *F17C 2223/0123* (2013.01); *F17C 2223/036* (2013.01); *F17C 2250/032* (2013.01); *F17C 2250/036* (2013.01); *F17C 2250/0439* (2013.01); *F17C 2250/0491* (2013.01); *F17C 2260/024* (2013.01); *F17C 2270/0168* (2013.01); *F17C 2270/0171* (2013.01);
(Continued)

(58) Field of Classification Search
USPC ........................................ 374/4, 1, 112, 166
See application file for complete search history.

(56) References Cited

U.S. PATENT DOCUMENTS

| | | | |
|---|---|---|---|
| 5,085,949 A | 2/1992 | Sanderson et al. | |
| 6,424,157 B1 | 7/2002 | Gollomp et al. | |
| 6,684,154 B2 * | 1/2004 | Isobe ................... | F02D 35/025 701/113 |

(Continued)

FOREIGN PATENT DOCUMENTS

| | | |
|---|---|---|
| KR | 10-0672273 B1 | 1/2007 |
| KR | 10-0837933 B1 | 6/2008 |

*Primary Examiner* — Mirellys Jagan
(74) *Attorney, Agent, or Firm* — Mintz Levin Cohn Ferris Glovsky and Popeo, P.C.; Peter F. Corless

(57) ABSTRACT

A method for managing a temperature anomaly in a hydrogen tank includes a temperature checking step for defining temperature values detected by temperature, a temperature comparing step for comparing the temperature values with each other and then checking whether there is a specific temperature difference among the temperature values, a temperature sensor judging step for judging the temperature sensor in which the specific temperature difference is generated as an abnormal temperature sensor, and judging the temperature sensor in which the specific temperature difference is not generated as a normal temperature sensor, and an abnormal temperature sensor managing step for applying the temperature value of the temperature sensor judged as the normal temperature sensor when the hydrogen tank in which the temperature sensor judged as the abnormal temperature sensor is provided is filled or amount of fuel in the hydrogen tank is calculated.

6 Claims, 3 Drawing Sheets

(51) Int. Cl.
*G01K 1/00* (2006.01)
*G01K 11/00* (2006.01)
*F17C 13/02* (2006.01)

(52) U.S. Cl.
CPC ............... *F17C 2270/0176* (2013.01); *F17C 2270/0178* (2013.01); *Y02E 60/321* (2013.01)

(56) References Cited

U.S. PATENT DOCUMENTS

| | | | |
|---|---|---|---|
| 6,953,630 | B2 | 10/2005 | Wells |
| 7,695,838 | B2 | 4/2010 | Komachiya et al. |
| 9,004,751 | B2 * | 4/2015 | Sakurada ............ F02D 41/1446 374/1 |
| 2003/0022038 | A1 | 1/2003 | Vaal et al. |
| 2005/0249992 | A1 * | 11/2005 | Bitoh ....................... B01B 1/005 429/423 |
| 2009/0081492 | A1 | 3/2009 | Hasuka et al. |
| 2011/0251825 | A1 * | 10/2011 | Nagoshi ................. F02D 41/222 702/183 |
| 2012/0032810 | A1 * | 2/2012 | Chillar .................. F01K 13/003 340/600 |
| 2014/0133516 | A1 * | 5/2014 | Ozaki ....................... G01K 7/22 374/1 |
| 2014/0234739 | A1 * | 8/2014 | Sachs .................. H01M 8/0432 429/433 |
| 2014/0376587 | A1 * | 12/2014 | Sakashita .............. B60W 10/08 374/1 |
| 2015/0078413 | A1 * | 3/2015 | Heinrich ............... F02D 41/222 374/1 |
| 2015/0362383 | A1 * | 12/2015 | Komiya ............ H01M 8/04373 702/99 |

* cited by examiner

METHOD FOR MANAGING TEMPERATURE ANOMALY IN HYDROGEN TANK, AND SYSTEM FOR MONITORING TEMPERATURES IN SAME

CROSS-REFERENCE TO RELATED APPLICATIONS

This application claims under 35 U.S.C. §119(a) priority to Korean Patent Application No. 10-2013-0139062, filed on Nov. 15, 2013, which is incorporated herein by reference in its entirety.

BACKGROUND (a) Field of the Invention

Exemplary embodiments of the present invention relate to a hydrogen tank (bombe), and particularly, to a method for managing a temperature anomaly in a hydrogen tank, which compares detected temperature values of a plurality of temperature sensors with each other and accurately checks whether a specific temperature sensor is abnormal to improve the reliability of the result of a control logic utilizing detected temperature values and secure the safety of a motor vehicle, and a system for the same.

(b) Description of Related Art

In general, since hydrogen that chemically reacts with oxygen is employed as fuel in a hydrogen fuel cell motor vehicle, a hydrogen storage system including a hydrogen tank (or bombe) is mounted to the motor vehicle.

In general, in view of a performance aspect, a high pressure of 700 bars is applied as an allowable pressure of the hydrogen tank, and a temperature between −40° C. and 85° C. is applied as an allowable temperature of the hydrogen tank. In particular, the temperature in the hydrogen tank should not exceed 85° C. for safety reasons when the hydrogen tank is filled with hydrogen.

For this reason, a temperature sensor for detecting internal temperature must be provided in the hydrogen tank.

Due to the above, a filling controlling logic utilizes the temperature value detected by the temperature sensor when the hydrogen tank is filled with hydrogen so that it is possible to secure a filling safety without exceeding a temperature of 85° C.

In addition, when calculating an amount of fuel, the logic for calculating amount of fuel utilizes the temperature value detected by the temperature sensor so that amount of fuel within the hydrogen tank can be accurately calculated. Since gaseous hydrogen fuel is stored in the hydrogen tank, the temperature value is utilized for calculating amount of fuel in the hydrogen tank.

However, a method utilizing the temperature value detected by the temperature sensor is applied to the filling controlling logic or the logic for calculating amount of fuel.

In this method, since it is overlooked that a temperature value is detected when the temperature sensor is abnormal as well as when the temperature is normal, it is possible that a result of the filling controlling logic and a result of the logic for calculating amount of fuel, which employ the temperature value, are inaccurate and/or unreliable.

As one example, the filling controlling logic controls a process for filling hydrogen with a constant temperature value of 85° C. or less provided by the abnormal temperature sensor so that safety cannot be secured when a filling process is performed.

In addition, since the logic for calculating amount of fuel calculates amount of fuel with a constant temperature value provided from the abnormal temperature sensor, an accuracy of amount of fuel in the hydrogen tank cannot be secured.

However, since the temperature sensor always generates a constant temperature value even in a failure state, there is a limit in judging accurately a failure of the temperature sensor, which can occur at any time.

In particular, even though a failure of the temperature sensor can occur while driving a motor vehicle, it is not verified whether the temperature sensor is normal or abnormal during driving so that this can result in an error in calculation of an amount of fuel.

SUMMARY

In view of the above, an object of the present invention is to provide a method for managing a temperature anomaly in a hydrogen tank, wherein detected temperature values of the temperature sensors provided in a plurality of hydrogen tanks, respectively, are monitored, the temperature sensor generating a temperature difference of 20° C. among the temperature values compared with each other is judged as being an "abnormal" temperature sensor, such that the temperature value of a temperature sensor judged as a "normal" temperature sensor is applied when the hydrogen tank in which the temperature sensor judged as the abnormal temperature sensor is provided is filled or when amount of fuel in the above hydrogen tank is calculated, so that the temperature value of the abnormal temperature sensor can be excluded from a filling controlling logic or the logic for calculating amount of fuel, and thus preventing the temperature from exceeding 85° C. at the time of filling the hydrogen tank. Further, calculation of an amount of fuel in the hydrogen tank can be accurately performed under any circumstance during driving of a motor vehicle, thus improving safety.

In order to achieve the above object, one embodiment of the present invention is directed to a method for managing a temperature anomaly in a hydrogen tank, comprising a temperature checking step for defining temperature values detected by temperature sensors provided in a plurality of hydrogen tanks, respectively, as T1, T2, T3 . . . Tn, respectively; a temperature comparing step for comparing the temperature values T1, T2, T3 . . . Tn with each other and then checking whether there is a specific temperature difference among the temperature values; a temperature sensor judging step for judging the temperature sensor in which the specific temperature difference is generated as the abnormal temperature sensor, and judging the temperature sensor in which the specific temperature difference is not generated as the normal temperature sensor; and an abnormal temperature sensor managing step for applying the temperature value of the temperature sensor judged as the normal temperature sensor when the hydrogen tank in which the temperature sensor judged as the abnormal temperature sensor is provided is filled or amount of fuel in the hydrogen tank is calculated, instead of the temperature value of the temperature sensor judged as the abnormal temperature sensor.

The specific temperature difference can be about 20° C.

In the temperature checking step, the temperature monitoring is performed while driving (i.e., during operation of) a motor vehicle.

Preferably, the temperature sensor in which the specific temperature difference is generated is displayed on a cluster of a driver's seat as a failure.

In addition, in order to achieve the above object, an embodiment of the present invention is directed to a system for monitoring temperature values in a hydrogen tank, comprising a plurality of temperature sensors provided in a plurality of hydrogen tanks, respectively, to detect temperatures of the hydrogen tanks, respectively; a controller monitoring temperature values detected by the plurality of temperature sensors, respectively, to judge the temperature sensor having a specific temperature difference as the abnormal temperature and applying the normal temperature value to a filling controlling logic or a logic for calculating amount of fuel, instead of a temperature value of the abnormal temperature sensor; and a displaying device provided on a cluster of a driver's seat to display the temperature sensor judged as a failure.

A pressure of 700 bars and an allowable temperature of −40~85° C. are applied to each of the plurality of hydrogen tanks and the specific temperature difference provided as a basis for judging whether the temperature sensor is abnormal is about 20° C.

DESCRIPTION OF SPECIFIC EMBODIMENTS

Figure 1:
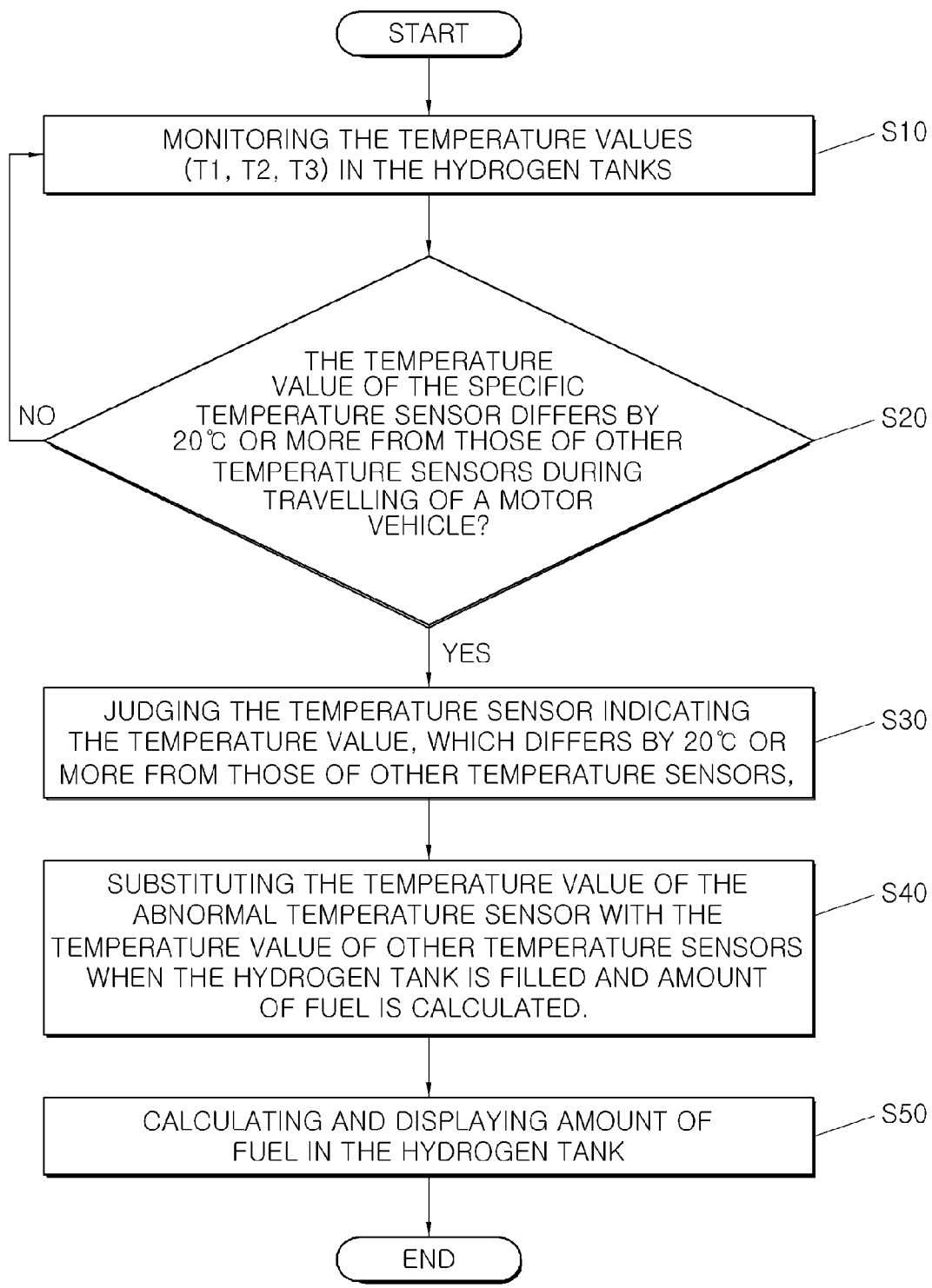
FIG. 1 is a flow chart illustrating a method for managing a temperature anomaly in a hydrogen tank in accordance with the present invention.

Exemplary embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Throughout the disclosure, like reference numerals refer to like parts throughout the various figures and embodiments of the present invention.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

FIG. 1 is a flow chart illustrating a method for managing a temperature anomaly in a hydrogen tank in accordance with the present embodiment. Below, this managing method is defined as logic for managing a failure of a temperature sensor.

As shown in FIG. 1, the logic for managing the failure of the temperature sensor is executed by monitoring a temperature in the hydrogen tank in step S10. An example of a system for the above method is exemplarily shown in FIG. 2.

Figure 2:
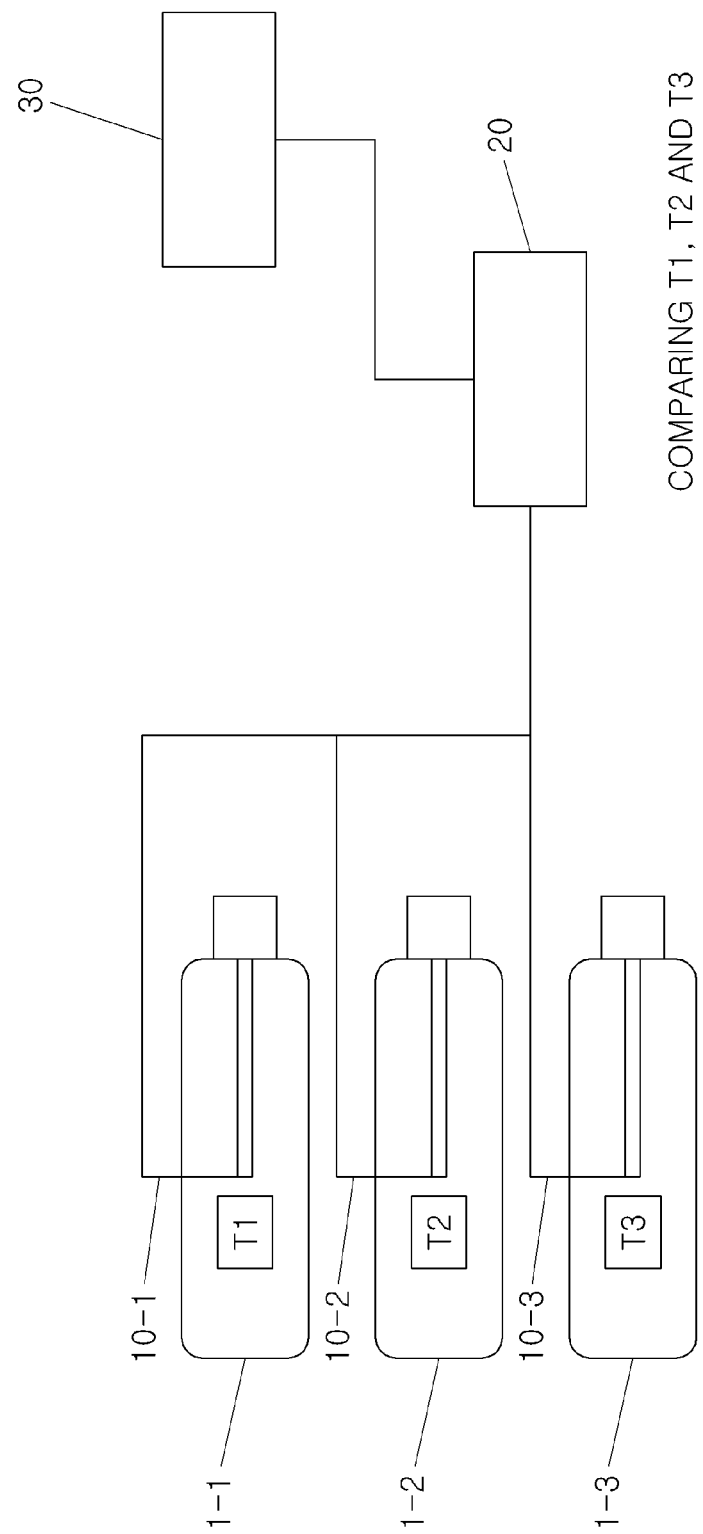
FIG. 2 is a schematic view of a system in accordance with the present invention.

As shown in FIG. 2, the system includes at least one or more hydrogen tanks 1-1, 1-2 and 1-3, at least one or more temperature sensors 10-1, 10-2 and 10-3, respectively, a controller 20 comparing detected temperature values with each other, and a displaying device 30 provided on a cluster of a driver's seat for enabling a driver to recognize the compared temperature values.

The hydrogen tanks 1-1, 1-2 and 1-3 includes the first, the second and the third hydrogen tanks 1-1, 1-2 and 1-3 forming one group, where a high pressure of 700 bars and an allowable temperature of −40~85° C. are applied to each of the first, the second and the third hydrogen tanks 1-1, 1-2 and 1-3.

The temperature sensors 10-1, 10-2 and 10-3 include the first, the second and the third temperature sensors 10-1, 10-2 and 10-3. The first temperature sensor 10-1 is installed in the first hydrogen tank 1-1, the second temperature sensor 10-2 is installed in the second hydrogen tank 1-2, and the third temperature sensor 10-3 is provided in the third hydrogen tank 1-3.

The controller 20 compares the temperature values detected by each of the temperature sensors 10-1, 10-2 and 10-3 with each other, judges whether one of the temperature sensors is an abnormal temperature sensor through the comparison, and excludes the temperature value of the judged abnormal temperature sensor from processes for controlling filling and calculating an amount of fuel.

The displaying device 30 displays a result of the judgment performed by the controller 20 to allow the driver to recognize a filling controlling status and an accurate amount of fuel.

Below, the logic for managing a failure of the temperature sensor is illustrated on the basis of the structure of the system.

The temperature monitoring for the hydrogen tank executed in step S10 is performed through the controller 20. For this purpose, the temperature values detected by the first, the second and the third temperature sensors 10-1, 10-2 and 10-3 installed in the first, the second and the third hydrogen tanks 1-1, 1-2 and 1-3, respectively, are input to the controller 20.

At this time, the temperature value detected by the first temperature sensor 10-1 is defined as T1, the temperature value detected by the second temperature sensor 10-2 is defined as T2, and the temperature value detected by the third temperature sensor 10-3 is defined as T3.

In step S20, a checking is performed to determine whether one of T1, T2 and T3 differs from the others. To this end, the controller 20 employs a specific temperature difference when comparing T1, T2 and T3 with each other.

As one example, the specific temperature difference of 20° C. is applied. Therefore, the temperature difference of T1-T2, the temperature difference of T1-T3 and the temperature difference of T2-T3 are compared with each other, and the controller checks whether the temperature value differs by 20° C. from the other temperature values on the basis of the above comparing result. As a result, the controller judges the specific temperature sensor among the first, the second and the third temperature sensors 10-1, 10-2 and 10-3, on which the temperature difference of 20° C. is generated.

Figure 3:
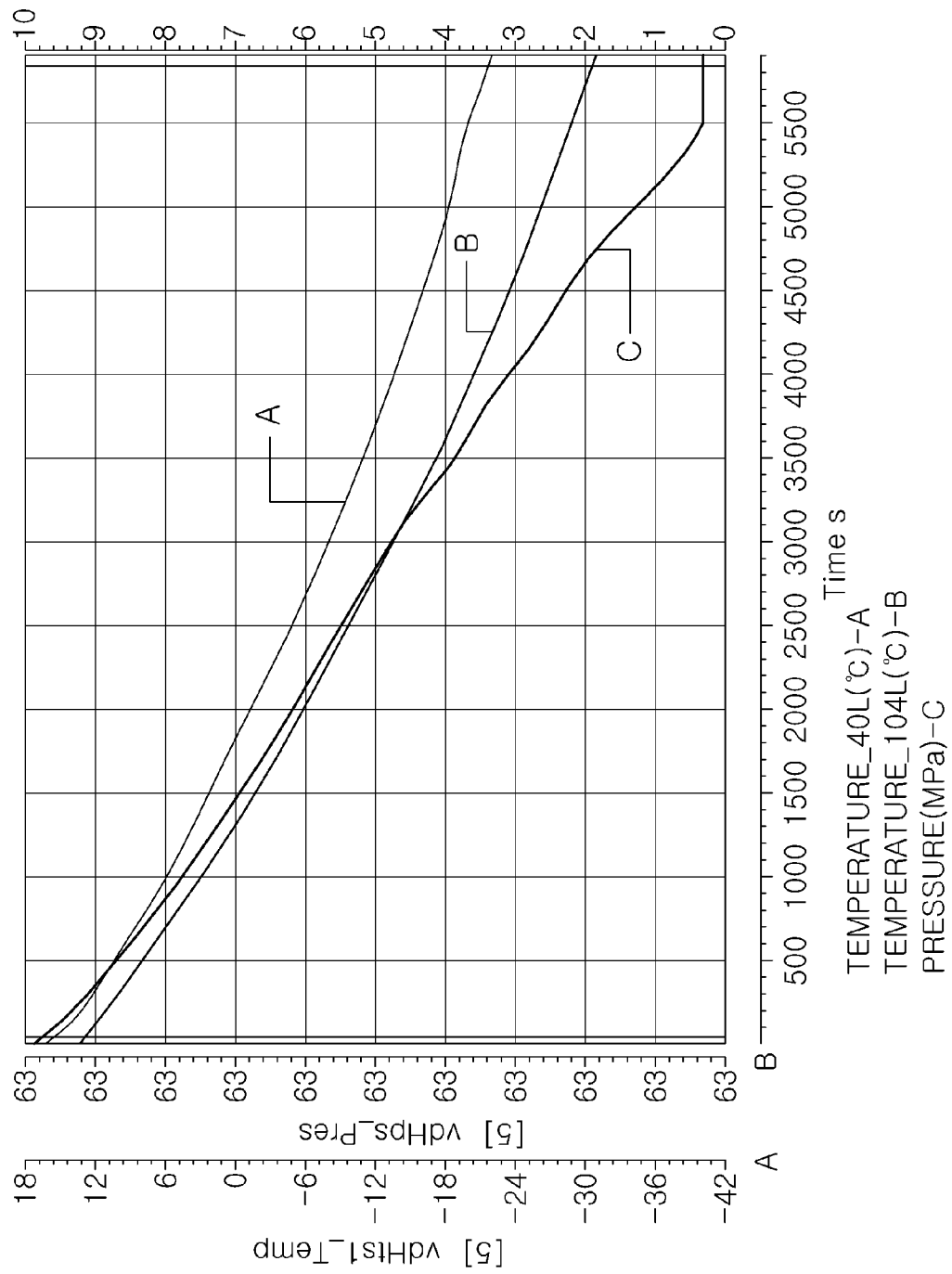
FIG. 3 is a graph showing an experimental example utilizing a temperature difference of about 20° C. at which a management for a temperature anomaly in a hydrogen tank in accordance with the present invention is carried out.

The basis for the above temperature difference of 20° C. is illustrated through an experimental example of FIG. 3. As shown in FIG. 3, the hydrogen tank (the first, the second and the third hydrogen tanks 1-1, 1-2 and 1-3 in the present embodiment) is the hydrogen tank to which a high pressure of 700 bars and an allowable temperature of −40~85° C. are applied, the temperature detection statuses of the first, the second and the third temperature sensors 10-1, 10-2 and 10-3 provided in the first, the second and the third hydrogen tanks 1-1, 1-2 and 1-3, respectively, are checked under the assumption of the worst case which can occur while driving a motor vehicle. It is possible to know a temperature range by which the temperature check results of the first, the second and the third temperature sensors 10-1, 10-2 and 10-3 can be judged as the temperature detection anomaly of the first, the second and the third temperature sensors 10-1, 10-2 and 10-3. This temperature range can be influenced by a dimension of each of the hydrogen tanks to which the first, the second and the third temperature sensors 10-1, 10-2 and 10-3 are installed. However, even though considering the temperature difference which can be caused by the dimension of the hydrogen tank, the temperature difference does not exceed 20° C. Therefore, the temperature difference of 20° C. is a temperature value which can be applied to an extreme case. In other words, by means of the temperature difference of 20° C. detected in the state that the first, the second and the third temperature sensors 10-1, 10-2 and 10-3 are normally operated, it is possible to judge that the first, the second and the third temperature sensors 10-1, 10-2 and 10-3 are in a normal state.

If the temperature sensor is abnormal, however, a temperature value detected by this temperature sensor is not changed, and in particular, a temperature difference which exceeds a normal temperature difference of approximately 20° C. is necessarily generated. Therefore, the temperature difference of approximately 20° C. can be effectively utilized for judging a failure of the temperature sensor.

In particular, the procedure of step S20 is always performed during stopping of a motor vehicle as well as operation of a motor vehicle.

In step S30, a case is shown in which any one of T1, T2 and T3 indicates the temperature difference of approximately 20° C. or more, and the temperature sensor indicating the temperature difference of approximately 20° C. or more is checked as an abnormal temperature sensor on the basis of the above. As one example, it is assumed that the first temperature sensor 10-1 among the first, the second and the third temperature sensors 10-1, 10-2 and 10-3 is abnormal.

Step S40 is the procedure in which the first temperature sensor 10-1 which is judged as the abnormal temperature sensor is excluded from being used, so as to not allow this sensor to be applied, and step S50 is the procedure in which a filling of the hydrogen tank or a calculation of amount of fuel is performed in a state where the first temperature sensor 10-1 which is judged as the abnormal temperature sensor is excluded. Due to the above, although the temperature sensor is considered abnormal, a filling safety is secured when the hydrogen tank is filled. In particular, a calculation of amount of fuel can be accurately performed.

As one example, in the case where the control is performed when the hydrogen tank is filled, if the first hydrogen tank 1-1 in which the first temperature sensor 10-1 which is judged as the abnormal temperature sensor is installed is filled together with the second and the third hydrogen tanks 1-2 and 1-3 in which the second and the third normal temperature sensors 10-2 and 10-3 are provided, respectively, the temperature of 85° C. is the reference temperature when the first hydrogen tank 1-1 is filled so that the temperature values detected by the second and the third normal temperature sensors 10-2 and 10-3 are applied to the first hydrogen tank 1-1 which is being filled with hydrogen. As a result, a safety of the filling controlling for the first hydrogen tank 1-1 in which the abnormal temperature sensor is provided can be secured.

This status is displayed on the displaying device 30 provided on the cluster of the driver's seat. Therefore, the driver can verify that the filling of hydrogen is controlled without exceeding the temperature of 85° C.

In addition, in the case where the control is performed for calculating amount of fuel in the hydrogen tank, the calculation of amount of fuel of the second and the third hydrogen tanks 1-2 and 1-3 utilizes the temperature values T2 and T3 detected by the second and the third normal temperature sensors 10-2 and 10-3. However, the calculation of amount of fuel of the first hydrogen tank 1-1 does not utilize the temperature value detected by the first temperature sensor 10-1 which is judged as the abnormal temperature sensor, but utilizes the temperature values T2 and T3 detected by the second and the third normal temperature sensors 10-2 and 10-3, instead of the temperature value T1. As a result, amount of fuel in the first hydrogen tank 1-1 is also accurately calculated.

This status is displayed on the displaying device 30 installed at the cluster of the driver's seat. Thus, the driver can verify that amount of fuel is always accurately calculated, and it is possible to resolve all inconvenience caused by an error of amount of fuel during travelling of a motor vehicle.

As described above, in the method for managing the temperature anomaly in the hydrogen tank in accordance with this embodiment, the detected temperature values T1, T2, T3 . . . Tn of the temperature sensors provided in a plurality of hydrogen tanks, respectively, are monitored, the temperature sensor in which the temperature difference of 20° C. among the temperature values compared with each other is generated is judged as the abnormal temperature sensor, and the temperature value of the temperature sensor which is judged as the normal temperature sensor is applied when the hydrogen tank in which the temperature sensor judged as the abnormal temperature sensor is provided is filled with hydrogen or amount of fuel of the hydrogen tank in which the temperature sensor judged as the abnormal temperature sensor is provided is calculated. Therefore the temperature value of the abnormal temperature sensor can be excluded from the filling controlling logic or the logic for calculating amount of fuel. In particular, the safety for the temperature exceeding 85° C. at the time of filling the hydrogen tank is secured and it is possible to accurately perform a calculation of amount of fuel in the hydrogen tank under any circumstance during travelling of a motor vehicle.

The present invention as described above is advantageous in that a failure of each of the temperature sensors installed in a plurality of hydrogen tanks, respectively, is accurately judged so that a reliability of the result of the control logic utilizing the detected temperature value is improved.

In addition, the present invention as described above is advantageous in that a failure of each of the temperature sensors provided in the plurality of hydrogen tanks, respectively, even while driving the motor vehicle, is accurately judged so that a stability of the motor vehicle is remarkably improved.

Furthermore, the present invention is advantageous in that the temperature value of the abnormal temperature sensor is not provided to the filling controlling logic controlling a hydrogen filling process without exceeding the temperature of 85° C. so that a safety of hydrogen filling is secured.

Also, the present invention is advantageous in that the temperature value of the abnormal temperature sensor is not provided to the logic for calculating amount of fuel so that amount of fuel is always accurately calculated.

In addition, the present invention is advantageous in that the failure of the temperature sensors provided in the plurality of hydrogen tanks, respectively, is checked by a software method without any hardware means so that the logic is improved and there is no burden on additional expense.

While the present invention has been described with respect to the specific embodiments, it will be apparent to those skilled in the art that various changes and modifications may be made without departing from the spirit and scope of the invention as defined in the following claims.

What is claimed is:

1. A method for managing a temperature anomaly in a hydrogen tank, comprising;
    a temperature checking step for defining temperature values detected by temperature sensors provided in a plurality of hydrogen tanks, respectively, as T1, T2, T3 . . . Tn, respectively;
    a temperature comparing step for comparing the temperature values T1, T2, T3 . . . Tn with each other and then checking whether there is a specific temperature difference among the temperature values;
    a temperature sensor judging step for judging the temperature sensor in which the specific temperature difference is generated as an abnormal temperature sensor, and judging the temperature sensor in which the specific temperature difference is not generated as a normal temperature sensor; and
    an abnormal temperature sensor managing step for applying the temperature value of the temperature sensor judged as the normal temperature sensor when the hydrogen tank in which the temperature sensor judged as the abnormal temperature sensor is provided is filled or an amount of fuel in the hydrogen tank is calculated, instead of the temperature value of the temperature sensor judged as the abnormal temperature sensor.

2. The method of claim 1, wherein the specific temperature difference is 20° C.

3. The method of claim 1, wherein monitoring of the temperature values in the temperature checking step is performed while driving a motor vehicle.

4. The method of claim 1, wherein the temperature sensor in which the specific temperature difference is generated is displayed on a cluster of a driver's seat as a failure.

5. A system for monitoring temperature values in a hydrogen tank, comprising;
    a plurality of temperature sensors provided in a plurality of hydrogen tanks, respectively, to detect temperatures of the hydrogen tanks, respectively;
    a controller monitoring temperature values detected by the plurality of temperature sensors, respectively, to employ a specific temperature difference when comparing temperature values of the plurality of temperature sensors with each other, to judge a specific temperature of the temperature sensor among the plurality of temperature sensors applying to a filling controlling logic or a logic for calculating an amount of fuel having a specific temperature difference as an abnormal temperature sensor and excluding a temperature value of the abnormal temperature sensor to the filling controlling logic or the logic for calculating an amount of fuel; and
    a displaying device provided on a cluster of a driver's seat to display the temperature sensor judged as a failure.

6. The system of claim 5, wherein a pressure of 700 bars and an allowable temperature of −40~85° C. are applied to each of the plurality of hydrogen tanks, and the specific temperature difference provided as a basis for judging whether the temperature sensor is abnormal is 20° C.

* * * * *